US012558021B2

(12) United States Patent
   Antonakis et al.

(10) Patent No.: US 12,558,021 B2
(45) Date of Patent: Feb. 24, 2026

(54) WRITING INSTRUMENT

(71) Applicant: BIC Violex Single Member S.A.,
   Anoixi (GR)

(72) Inventors: Ion-Ioannis Antonakis, Anoixi (GR);
   Anargyros Karakalas, Anoixi (GR);
   Dimosthenis Tsagkrasoulis, Anoixi
   (GR); Nikolaos Chrysanthakopoulos,
   Anoixi (GR)

(73) Assignee: BIC Violex Single Member S.A.,
   Anoixi (GR)

( * ) Notice: Subject to any disclaimer, the term of this
   patent is extended or adjusted under 35
   U.S.C. 154(b) by 272 days.

(21) Appl. No.: 18/482,627

(22) Filed: Oct. 6, 2023

(65) Prior Publication Data

US 2024/0115188 A1     Apr. 11, 2024

(30) Foreign Application Priority Data

Oct. 7, 2022    (EP) ..................................... 22200178

(51) Int. Cl.
   *A61B 5/00*          (2006.01)
   *A61B 5/11*          (2006.01)
   (Continued)
(52) U.S. Cl.
   CPC .......... *A61B 5/4082* (2013.01); *A61B 5/1101*
   (2013.01); *A61B 5/1114* (2013.01);
   (Continued)
(58) Field of Classification Search
   CPC ................ A61B 5/1101; A61B 5/4082; A61B
   5/1114; A61B 5/225; A61B 5/6825; A61B
   5/124; A61B 5/389
   See application file for complete search history.

(56) References Cited

U.S. PATENT DOCUMENTS

| | | | | |
|---|---|---|---|---|
| 2012/0172682 A1* | 7/2012 | Linderman | ............ | A61B 5/389 |
| | | | | 600/300 |
| 2013/0060124 A1* | 3/2013 | Zietsma | ............... | A61B 5/1101 |
| | | | | 600/407 |
| 2018/0356890 A1* | 12/2018 | Zhang | ..................... | G06F 3/014 |

FOREIGN PATENT DOCUMENTS

KR        20190023423 A        3/2019

OTHER PUBLICATIONS

F. Lunardini et al., "A Smart Ink Pen for the Ecological Assessment
of Age-Related Changes in Writing and Tremor Features," in IEEE
Transactions on Instrumentation and Measurement, vol. 70, pp.
1-13, 2021, Art No. 4002613, doi: 10.1109/TIM.2020.3045838.

(Continued)

*Primary Examiner* — Sana Sahand
(74) *Attorney, Agent, or Firm* — Bookoff McAndrews,
PLLC

(57)               ABSTRACT

The present disclosure relates to a computer-implemented
method for monitoring hand movements of a writing instru-
ment's user, comprising: providing an electromyography
sensor on the user's wrist or hand; monitoring hand move-
ments of the user during a writing session with the writing
instrument by reading sensors of the writing instrument;
monitoring hand muscle activity of the user during the
writing session by reading the electromyography sensor;
correlating hand motion data and hand muscle data obtained
from the monitoring; evaluating the correlated data and
classifying the hand movements as normal or abnormal
based on at least one of tremor parameters, hypokinetic
parameters, and historical data of the user; and providing an
indication in case of an abnormal evaluation.

20 Claims, 3 Drawing Sheets

(51) Int. Cl.
    *A61B 5/22*       (2006.01)
    *A61B 5/389*     (2021.01)

(52) U.S. Cl.
    CPC .............. *A61B 5/225* (2013.01); *A61B 5/389*
           (2021.01); *A61B 5/4088* (2013.01); *A61B*
           *5/681* (2013.01); *A61B 5/6824* (2013.01);
           *A61B 5/6825* (2013.01); *A61B 2562/0219*
           (2013.01); *A61B 2562/0247* (2013.01)

(56)              References Cited

OTHER PUBLICATIONS

Samantha O'Sullivan, Niall Murray, and Thiago Braga Rodrigues. 2022. The design and evaluation of a wearable-based system for targeted tremor assessment in Parkinson's disease. In Proceedings of the 13th ACM Multimedia Systems Conference (MMSys '22). Association for Computing Machinery, New York, NY, USA, 304-309. https://doi.org/10.1145/3524273.3532902.
Search Report issued in European Application No. 22200178, mailed on Mar. 23, 2023.

* cited by examiner

| User holds pen to perform handwriting | 200 |
| User wears EMG band | 210 |
| Pen sensors detect hand movements | 220 |
| EMG sensor measures hand muscle activity | 230 |
| Algorithm fuse sensor data | 240 |
| Algorithm calculates hand movement properties related to tremor and hypokinetic movement | 250 |
| Algorithm evaluates hand movement properties and alerts user | 260 |

WRITING INSTRUMENT

CROSS REFERENCE TO RELATED APPLICATION

This application claims priority from European patent application EP22200178.6, filed on Oct. 7, 2022, its contents being incorporated herein by reference.

TECHNICAL FIELD

The present disclosure relates to a method for monitoring hand movements of a writing instrument's user and a system for monitoring hand movements of its user.

BACKGROUND

Alzheimer's Disease (AD) is a form of dementia, a neurodegenerative disease of the brain. The disease process is associated with amyloid plaques, neurofibrillary tangles, and loss of neuronal connections in the brain. Unfortunately, the cause of Alzheimer's disease is poorly understood. There are many environmental and genetic risk factors associated with it. The strongest genetic risk factor is from an allele of APOE gene. Other risk factors are history of head injury, clinical depression, and high blood pressure.

Parkinson's disease (PD) is a long-term degenerative disorder of the central nervous system that mainly affects the motor system. The cause of PD is unknown, with both inherited and environmental factors believed to play a role. The symptoms are due to the death of cells in the substantia nigra, a region of the midbrain, leading to a dopamine deficit. The cause of this cell death is poorly understood but involves the build-up of misfolded proteins into Lewy bodies in the neurons.

Both AD and PD are associated with movement disorder symptoms. AD is associated with reduced arm rigidity and longer airtime during handwriting. PD is associated with resting tremor, bradykinesia and reduced rigidity.

Movement disorders (MD) including Hand movement disorders encompass disorders characterized by involuntary movements and/or loss of control or efficiency in voluntary movement. Two main categories of movement disorder phenomena can be distinguished. The first corresponds broadly to akinetic-rigid disorders, the second to hyperkinetic disorders. The hyperkinetic disorders can be separated into two main subdivisions, one in which the movements have a jerky character, and a second in which this jerky character is absent.

By definition, tremor is characterized by involuntary, rhythmic and sinusoidal alternating movements of one or more body parts. The movement does not necessarily involve a limb, as tremor can affect almost any body part, including the head, chin and soft palate.

The keyword in identifying tremor is 'rhythmicity'; that is, the oscillations occur at a regular frequency. Identifying rhythmicity with the naked eye is not always easy, however, because despite having a fixed frequency, tremors often have a variable amplitude. Such changes in amplitude with time can occur spontaneously but might also result from movements or changes in posture assumed by the patient, or from emotion and fatigue. Despite the amplitude change, tremor frequency remains unchanged. In patients who show changes in tremor amplitude, objective and quantitative tremor registration, by use of electromyography and accelerometers, can confirm rhythmicity.

Tremors can be classified in various ways. One important classification system is based on the characteristic moment or situation of occurrence.

A resting tremor can only be definitively identified when the affected body part is not actively moving, and when the effect of gravity is removed completely. Resting tremor usually disappears during voluntary actions. Sometimes, eye closure or distraction is needed to provoke the resting tremor (for example, asking the patient to count backwards while they are sitting with their arms resting on the arms of a chair).

Occasionally, the tremor is only seen in the arm when the individual is walking ('dependent tremor'). The resting tremor can be highly focal; for example, tremor in Parkinson's Disease might begin in a single digit. A common diagnostic pitfall is failure to recognize that resting tremors can occur in any position assumed by the affected body part, even when this involves a posture that is actively maintained against gravity (thereby mimicking a 'postural tremor').

For example, the typical resting tremor in the hands of patients with PD can also be observed when the arms are stretched out in front of the individual. In this case, distinction between postural tremor (as in essential tremor) and true resting tremor can be accomplished by carefully examining how rapidly the tremor becomes manifest after the new posture has been assumed, immediately in case of postural tremor, but after a delay of several seconds in the case of resting tremor (a phenomenon termed 'resetting' or 're-emergent tremor'). The frequency of a resetting tremor is the same as that observed in the rest position.

Kinetic tremors occur during volitional movements. a distinction is made between simple or action tremor (evident during a target-directed movement), terminal tremor (evident at the end of a target-directed movement) and intention tremor (which increases progressively in amplitude throughout the movement until the intended target is reached).

Isometric tremor occurs when muscles forcefully contract without shortening; for example, while pushing against a wall.

Finally, psychogenic tremor is characterized by a variable frequency, direction and amplitude, as well as by distractibility.

Patients with PD, for example, not only have resting tremor, but commonly also show a postural tremor with a higher frequency.

The frequency and amplitude of a tremor vary to the degree that the tremor may be hardly noticeable or severely disabling. Frequency can be divided into three categories of oscillations per second: slow (3 to 5 Hz), intermediate (5 to 8 Hz) or rapid (9 to 12 Hz). Amplitude may be classified as fine, medium or coarse, depending on the displacement produced by the tremor about the fixed plane. A coarse tremor has a large displacement, whereas a fine tremor is barely noticeable.

The tremor in Parkinson's disease occurs at rest and is characterized by a frequency of 4 to 6 Hz and a medium amplitude.

We not only define akinesia as an umbrella term for a symptom complex that can include bradykinesia (slowness of movement) and hypokinesia (poverty of movement, and movements that are smaller than intended), but also—crucially and fundamentally—as the progressive fatiguing and decrement of repetitive alternating movements seen during finger or foot tapping.

To identify bradykinesia, doctors ask the patient to make large, regular, repetitive alternating movements of each extremity in turn: opposition of the thumb to the crease between the terminal phalanges of the index and third fingers, and repeatedly tapping the forefoot on the floor, keeping the heel on the ground. It is easy to see—or, at the ankle, hear—early progressive reduction in amplitude or speed of the movements.

For the diagnosis of parkinsonism, bradykinesia is defined as including fatiguing and decrement of repetitive alternating movements.

A movement smoothness parameter can be used as a Parkinson's disease bradykinesia descriptor. Smoothness can be measured using the spectral arch length (SAL) of movement speed profile as an appropriate index of movement fluidity. SAL can account for the change in the number of submovements and the inter-submovement interval, which are movement features influenced by bradykinesia. To compute smoothness it is not necessary to filter data because of the inherent low-pass filtering action performed. Specifically, SAL can be computed within the frequency range 0-4 Hz of the speed profile in each movement cycle and in each single movement. Spectral arch length estimates movement smoothness by calculating the arc length of the magnitude of the Fourier Spectrum of a given speed profile within a frequency range.

The present disclosure addresses the problems detecting medium to severe symptoms of a chronic or neurodegenerative disease which may be expressed by the quality of handwriting. Further, fine hand movements being indicative of such symptoms cannot be easily detected with high accuracy by now.

SUMMARY

In a first general aspect, the present disclosure relates to a computer-implemented method of a writing instrument's user, comprising:

providing an electromyography, EMG, sensor on the user's wrist or hand;
  monitoring hand movements of the user during a writing session with the writing instrument by reading sensors of the writing instrument;
  monitoring hand muscle activity of the user during the writing session by reading the EMG sensor;
  correlating hand motion data and hand muscle data obtained from the monitoring;
  evaluating the correlated data and classifying the hand movements as normal or abnormal based on at least one of tremor parameters, hypokinetic parameters, and historical data of the user; and
  providing an indication in case of an abnormal evaluation.

In embodiments, the method may comprise storing monitored data and/or related statistics as historical data.

In embodiments, monitoring hand movements may include monitoring at least one of a writing force between the writing instrument's tip and a writing surface, motion information including position, orientation, speed, and/or acceleration of the writing instrument, and a force distribution and/or gripping strength applied by the user's fingers on the writing instrument.

In the present disclosure the terms "strength", "force", and "pressure" may be interchangeably used. The terms "gripping force", "gripping force", and "gripping pressure" name quantities which can be directly obtained from such a sensor.

In embodiments, monitoring hand movements may include extrapolating a time span of the writing instrument not in contact with the writing surface between two consecutive writing strokes from the monitored writing force.

In embodiments, monitored data may be aggregated into motion profiles of the hand movements, wherein the motion profiles are at least one of position, speed, or acceleration of the writing instrument.

In embodiments, correlating and evaluating data may include computation of an average speed of the writing speed profile of writing identical words or sentences multiple times during a writing session.

In embodiments, correlating may include fusing hand motion data through a data processing algorithm, wherein the hand motion data has the form of a 3-dimensional vector, wherein the dimensions are position, speed, and acceleration of the writing instrument. The data processing algorithm may include or consist of a Kalman filter.

The hand motion data may have the form of a 3-dimensional vector or array. The vector or array may also have 2 or more than three dimensions.

In embodiments, the method may comprise sorting the fused hand motion data into writing and non-writing parts by using data of a writing force between the writing instrument's tip and a writing surface. The writing force may also be named applied force.

In embodiments, evaluating may include identifying at least one of tremor frequency, direction, and amplitude by performing a frequency domain analysis from at least one of x, y, and z directions on the writing parts of the fused hand motion data; performing a frequency domain analysis on root mean square and/or zero crossings features extracted from the hand muscle data; and computing a weighted average of the primary frequency by combining the variables obtained by the two prior steps. The frequency domain analysis may include or consist of a Fourier analysis.

In embodiments, evaluating may include quantifying the duration of the non-writing parts; and fitting a regression model to a non-writing duration.

In embodiments, the indication may be provided via a wireless communication system to an external device having an interface.

In a second general aspect, the present disclosure relates to a system for monitoring hand movements of its user, comprising:

a writing instrument comprising: one or more sensors configured to monitor hand movements of the user during a writing session with the writing instrument by reading sensors of the writing instrument; a communication system configured to provide an indication in case of abnormal hand movements; and a computer system configured to execute the computer-implemented method for monitoring hand movements of a writing instrument's user as described above; and
  an electromyography, EMG, sensor configured to be attached on the user's wrist or hand, wherein the EMG sensor is in communication with the writing instrument.

In embodiments, the system may comprise a storage system configured to store generated data as historical data.

In embodiments, the system may comprise at least one of:
  a hand presence sensor configured to obtain a force distribution and/or a gripping strength applied by the user's fingers on the writing instrument;
  a force tip sensor configured to obtain a writing force between the writing instrument's tip and a writing surface;
  at least one motion sensor configured to obtain at least one of position, orientation, speed, and acceleration of the writing instrument; and a proximity sensor configured to obtain a hovering distance of the writing instrument's tip above the writing surface.

In embodiments, the proximity sensor may be a time-of-flight sensor, wherein the hand presence sensor comprises a plurality of flexible pressure sensing pads, wherein the force tip sensor comprises a force and/or pressure sensor configured to measure a force and/or pressure of a tip of the writing instrument, and/or wherein the at least one motion sensor comprises at least one of a magnetometer, a gyroscope, an accelerometer, and an inertial measurement unit.

In embodiments, the writing instrument may comprise a user interface configured to receive input from a user and/or to provide information to the user such as the indication.

According to examples of the present disclosure, abnormal hand movement symptoms associated with neurodegenerative diseases can be detected early with the use of a system comprised of a multifunctional pen equipped with several motion detection sensors and an EMG band. Hand/finger Tremor and hand hypokinetic movements, such as bradykinesia, are key characteristics of hand movement disorders that could be identified by the present disclosure.

A writing instrument of the present disclosure e.g., a smart pen is capable of both being used as a conventional writing instrument, i.e., write or sketch on a writing surface, as well as capture and process data associated with the handwriting/sketching operation.

Surface EMG electrodes can be placed over the palm/hand intrinsic muscles as an extension of the writing instrument. Their data are linked and synchronized to the sensor position and force data of the writing instrument.

The fusion of collected hand movement data from writing instrument's sensors and electrodes may be leveraged to provide high accuracy hand movement information leading to indications of the early identification of handwriting and/or sketching deterioration.

In Parkinson's disease, action tremor is present in nearly half of patients when drawing. This tremor is characterized by a sinusoidal pattern of periodicity, unidirectional axis, constant amplitude and frequency and no modification in writing force. In order to identify and differentiate this tremor type from other movement disorders (high specificity and sensitivity) during handwriting sessions, it is proposed to combine motion and force and/or pressure information.

Writing force, i.e., the force between pen's tip and the writing surface, can be quantified via a force sensor in the smart pen tip.

Motion information may comprise of position, orientation, speed (translational and rotational), acceleration (translational and rotational) of the pen and the writing hand of the user. These data may be captured by a combination of sensors, namely a magnetometer, one or more IMU, a flexible pressure sensing pad located in the pen's holding area and finally a flexible EMG sensor on the user's wrist or hand.

The magnetometer yields absolute positional and orientation information, which can be differentiated to yield speed and acceleration. The IMU provides speed and acceleration data. The flexible sensing pad measures force distribution applied by the fingers on the pen's body. This force is analogous to the acceleration forces applied to the pen. Finally, the EMG sensor quantifies the frequency of muscle contraction and extension.

These four sources of data can be fused in order to yield accurate motion profiles of the handwriting movements. The profiles may be either position, speed or acceleration, or a combination of the above. This is due to the periodic and sinusoidal nature of the examined tremor, which has the same pattern irrespective of how it is quantified (position, speed or acceleration).

The same data can also assist in the diagnosis of Alzheimer's Disease or Mild Cognitive Impairment. It has been shown that during writing, pen speed and acceleration, as well as writing force are predictive features for these diseases. The same holds true for pen gripping strength. The combination of these two sources increases the discriminate nature of the computational analysis.

Coming back to Parkinson's disease, another major indication during handwriting is bradykinesia. Bradykinesia is primarily characterized by a progressive decrease in writing speed. To quantify the progressive deterioration of writing speed using the smart pen device, the written text needs to be captured in a digital format. Analysis then includes the computation of the writing speed profile average speed of writing the same word/sentence multiple times during a session.

Additionally, the non-writing time i.e., pen tip is in the air, further strengthens the results. A gradual increase in non-writing time is also an indication of the issue. The above measurements can be acquired via the same data and sensors described above. A magnetometer, assisted by an IMU (sensor fusion) yields the pen tip positional data and further speed information, while a tip force sensor allows for identifying the non-writing (on-air) time. In this case, the force sensor may be substituted by a Time-of-Flight (TOF) sensor, since we are not interested in the actual writing force, but only whether the pen tip touches the writing surface or not.

Steps of an example method of the present disclosure may be as follows:

The user holds the writing instrument or smart pen with his hand for handwriting or sketching action.

The user wears an EMG hand band which is linked to the smart pen and/or its sensors.

The user starts to perform handwriting/sketching action.

Smart pen and EMG sensors detect hand movements and respective muscle activity in tandem and with high accuracy.

Algorithms analyze motion profile, correlate motion and muscle sensor data, extract key metrics and calculate tremor and hypokinetic hand movement properties.

An algorithm evaluates tremor and hypokinetic parameters and classifies the handwriting and/or sketching motion as normal or abnormal.

The system alerts the user.

An example system of the present disclosure may provide the following features:

A multifunctional writing instrument capable of detecting fine hand movements such as tremor or hypokinetic movement, using a set of sensors incorporated in it, measuring e.g. the force applied by the user on the writing surface, the gripping pressure, the absolute position of the pen in space, its motion during operation as well as on-air.

A flexible smart pen extension module equipped with EMG electrodes, linked to the smart pen, capable of measuring hand muscle activation.

A position detecting sensor embedded on the pen body, like magnetometer, IMU.

A hand presence detection sensor embedded on the pen body, like a gripping force sensor.

A writing action detection sensor embedded on the pen tip, like a tip force sensor.

A microcontroller in the smart pen for the control of the sensors, a memory unit for storing sensor data, a communication unit for transferring the logged data, a power source for the system, and at least one LED for indicating key operational statuses.

A set of algorithms used for data collection, data fusion, hand movement properties and muscle activity (like tremor and hypokinetic movement) analysis, calculation and evaluation.

A dedicated software application for historical data storage, analysis, user interface and communication.

Particular examples of the first to second general aspects can be implemented so as to realize one or more of the following advantages.

First, a system is provided to measure and quantify fine hand movements and hand muscle activity with high accuracy and resolution during the use of a pen for trivial handwriting activities without any disturbance of the user.

Second, the present disclosure enables to measure the source of hand movement disorders e.g., muscle disorder and combine data with the resulting hand position, acceleration, vibration parameters measured by other sensors.

Third, the present disclosure enables to combine and fuse sensor data to increase hand movement detection resolution and accuracy.

Fourth, the present disclosure enables to calculate hand movement properties related to hand tremor and hypokinetic movement related with neurodegenerative diseases like Parkinson's and Alzheimer's.

Fifth, the present disclosure enables to alert the user whether his hand movements during handwriting are normal or abnormal.

The present disclosure allows identifying a chronic or degenerative disease in early stages which is very difficult in most cases.

The present disclosure allows to detect the quality of handwriting which may be severely affected when medium to severe symptoms of a chronic or neurodegenerative disease are expressed.

The present disclosure allows detection of fine hand movement which cannot be easily detected with high accuracy with one or a few standalone sensors.

The present disclosure overcomes issues when position and movement sensors measure the result of hand movement disorders and not the source. The present disclosure allows to distinguish between movements associated with unintentional muscle activity and intentional motions, such as when someone plays with the pen.

The present disclosure overcomes issues in that most diagnostic tests currently adopted for AD, PD and MCI require that the patient visits a dedicated facility where he/she might be subjected to complex and expensive tests performed by trained health-care professionals. The present disclosure allows detection without this process, which is time-consuming, could be stressful for the patient as well as costly.

Regarding smart pen hand movement detection sensors the implementation of smart, wearable sensors and systems in almost any device is possible due to the low power consumption, minimal obtrusiveness, and low weight. Several sensing technologies can be implemented independently or in tandem to capture the writing motor skills of a person while using a writing instrument such as a pen, pencil, marker or stylus.

A non-exhaustive list of the sensors considered for a smart pen or digital writing instrument is provided below:

Flexible pressure sensing pads can capture the gripping strength of the user and any potential fluctuation due to tremor, use of flexible pressure sensors is essential in order to fit the tubular-like shape of most writing instruments. Monitoring the gripping strength throughout a handwriting session enables also the determination of fatiguing and decrement of repetitive movements.

Force and/or pressure sensors are sensors, along with strain gauges when placed inside the writing instrument which allow for measuring the force applied between the pen's tip and the writing surface. Handwriting and sketching forces have been considered of diagnostic value for patients with mild cognitive impairment. Force and/or pressure sensors may also be implemented to detect or measure a gripping strength of the user.

Accelerometers, gyroscopes, or their combination, i.e., in the form of Inertial Measurement Units (IMU) are used for tremor analysis as well as other parameters for patient classification. These types of sensors enable the determination of the writing speed, which is considered as a metric for identifying bradykinesia or other hypokinetic hand movement symptoms, like dyskinesia, dystonia and motor fluctuations.

Magnetometers can be used in a smart pen to measure the writing angle between the writing instrument and the writing plane or surface. Tracking of the pen's orientation and/or direction enables the assessment of the user's hand rigidity and tremor.

Time of Flight (ToF) proximity sensors can be involved in the tracking the inter-foot distance during walking. This setup can be reconfigured to track the hovering distance of the pen during writing. Longer on-air times may indicate deterioration in a person's cognitive skills.

Electromyography (EMG) measures muscle response or electrical activity in response to a nerve's stimulation of the muscle. The test is used to help detect neuromuscular abnormalities. During the test, one or more small electrodes are inserted through the skin into the muscle. The electrical activity picked up by the electrodes is then displayed on an oscilloscope. An audio-amplifier is used so the activity can be heard. EMG measures the electrical activity of muscle during rest, slight contraction and forceful contraction. Muscle tissue does not normally produce electrical signals during rest. When an electrode is inserted, a brief period of activity can be seen on the oscilloscope, but after that, no signal should be present.

After an electrode has been inserted, the user may be asked to contract the muscle, for example, by lifting or bending a leg. The action potential (size and shape of the wave) that this creates on the oscilloscope provides information about the ability of the muscle to respond when the nerves are stimulated. As the muscle is contracted more forcefully, more and more muscle fibers are activated, producing action potentials.

The present disclosure employs surface electromyography sensors for hand movements detection. The various types of wearable sensors proposed in the literature for the measurement and assessment of the arm and/or hand movements are accelerometers, gyroscopes, magnetic sensors, force sensors, and inertial sensors. However, these sensor systems only modestly contribute to the arm and/or hand movement assessment. Specifically, the use of one or two isolated sensors in motion acquisition restricts the movement quantification, due to the limited amount of the collected data.

More informative sensors are the ones that measure muscle activity, like the skin surface Electromyography (EMG) electrodes, which detect the electrical potential generated by muscles. The main drawback of the standard EMG electrodes is the wired connection with a device for EMG signal representation. Consequently, muscle activity tests are available only in the hospital environment.

Parkinson's disease symptoms change the EMG signal properties and suggest that EMG analysis is able to detect differences between the deep brain stimulation settings. EMG data, can be used along with the readings from the accelerometer, to successfully differentiate essential tremor from Parkinson's disease. It has been achieved to obtain reliable EMG data related to arm/hand movements from measurements acquired with a wireless wearable armband device.

The armband electromyographic sensor is worn on the forearm and collects the data from the four groups of muscles-flexors, extensors, internal, and external forearm muscles. One very important conclusion is that external forearm muscles of both hands in PD patients have demonstrated the lowest performance of all forearm muscles in the sense of the muscle activity compared with a control group. This result suggests that external forearm muscles are the most affected by the Parkinson's disease.

Collected sensor data have revealed the bradykinesia patterns in patient movement data. The slowness of the movement and sequential drop of the amplitude over time (so-called "sequence effect") are visible from temporal evolution. Such results indicate the potential of the proposed system to be used by therapists for quantitative assessment of bradykinesia as well as tracking of its evolution and potentially the patient's response in medication.

The skeletal muscles of the hand are responsible for the movement of the hand and fingers. These muscles subdivide into two groups: the extrinsic and intrinsic muscles. The extrinsic muscle group is called so because the muscle belly originates in the forearm.

The intrinsic muscle groups consist of smaller muscles solely located within the various hand osseofascial compartments within the anatomic confines of the wrist (proximally) and phalanges (distally). The intrinsic muscles are important for various hand functions, such as pinch and grip strength.

An understanding of the intrinsic hand muscle groups is crucial, as denervation and loss of function may lead to pronounced deficits in hand function.

Regarding writing action, handwriting is the writing action done with a writing instrument, such as a pen or pencil, using the hand. Handwriting includes both printing and cursive styles. Handwriting involves the use of a pen or pencil which the user keeps holding with his hand/fingers even when he does not write. At a writing session the user writes or sketches with a writing instrument. A writing session includes actual handwriting instances and on-air instances in which a tip of the writing instrument is not touching a writing surface.

Because each person's handwriting is unique and different, it can be used to verify a document's writer. Significant changes or the deterioration of a person's handwriting may be a symptom or a result of several different diseases.

The normal pen grip may be performed in the following way:
- the writing instrument is held in a stable position between the thumb, index and middle fingers,
- the ring and little fingers are bent and rest comfortably on the table,
- the index finger and thumb form an open space,
- the wrist is bent back slightly, and the forearm is resting on the table, the writing instrument is held about 1-2 cm from the tip.

So, especially while writing, a user exerts a gripping force on the body of the pen.

Certain terms are used in the following manner in the present disclosure:

The expression "digital device" may refer to an electronic device that uses discrete, numerable data and processes for all its operations, and is capable of displaying content to the user. Examples of such a device include but are not limited to: Mobile phones, Laptops, Tablets, Personal computers, Netbooks, etc.

The expression "haptic or tactile feedback" may refer to a physical response on a digital device from the user input, also known as kinaesthetic communication. The application with mechanical or electronic means of force, vibrations, or motions to the user in response to a user's action on the digital device.

The expression "human machine interface" may refer to a user interface or dashboard or an input system that connects a person to a machine, system, or device. For example, a physical button on a remote controller.

The expression "group of users" may refer to a panel of users selected through specific methodology, with the scope to test products and provide feedback, in order to provide statistical insights to specific parameters of the products and their respective use.

DETAILED DESCRIPTION

Figure 1:
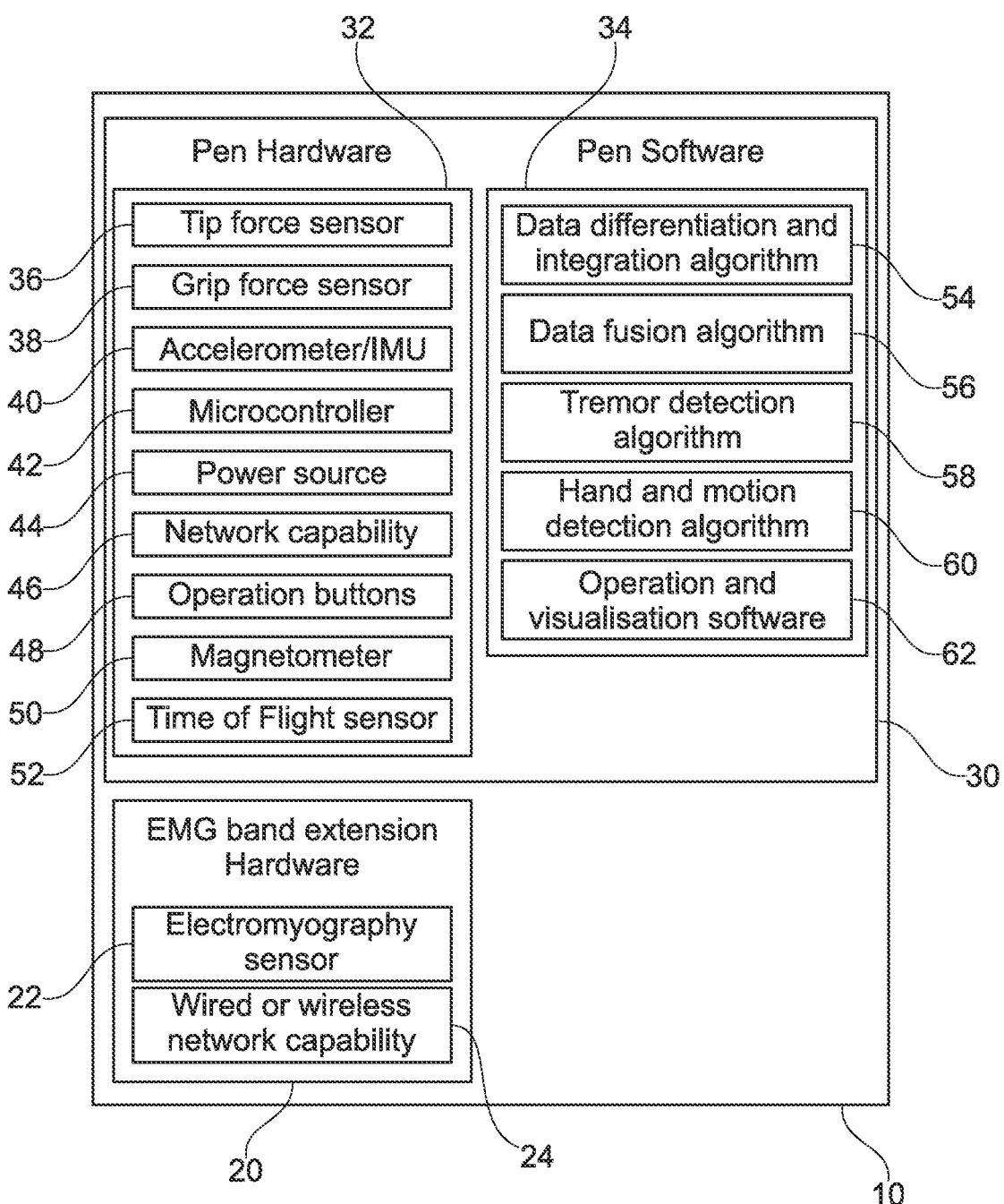
FIG. 1 illustrates an overview of components of a system for monitoring hand movements of its user according to the present disclosure.

FIG. 1 shows an overview of components of a system 10 for monitoring hand movements of its user according to the present disclosure. The system 10 includes an electromyography, EMG, unit 20 and a writing instrument 30. The writing instrument 30 can be named smart pen, digital writing instrument or digital device. The writing instrument 30 includes the pen hardware 32 and the pen software 34.

In examples, the system may also be named as the hand movement disorders system capable of measuring hand movements of a user during handwriting and evaluating if there is any abnormality. The hand movement disorders system includes or consists of two subsystems i.e., a hand movement detection writing instrument or smart pen system and a hand movement disorder evaluation software. The hand movement detection smart pen system is capable of detecting hand movement parameters like position, direction, acceleration and muscle activity with sensors incorporated or connected to the smart pen.

In this configuration, the electromyography, EMG, unit is part of the writing instrument. The hand movement disorder evaluation software can be part of the writing instrument or of a further digital device.

As shown in FIG. 1, the pen hardware 32 of the writing instrument 30 includes a tip force sensor 36 or writing surface contact sensor.

One or more force and/or pressure sensor and/or strain gauge is placed inside the body of the writing instrument, either aligned with the longitudinal axis of the pen or at an inclined configuration, to record the developed force between the nib the writing surface during the handwriting operation.

In embodiments, a force/pressure sensor may have at least 0.01 N resolution, measure up to 10 N of force and be capable of identifying 4086 pressure levels or more.

In embodiments, the size of the force/pressure sensor may be no more than 2.5×2.5×1.0 mm in order to fit inside the writing instrument and be placed along its longitudinal axis or at an inclined configuration without affecting the ergonomics of the writing instrument.

In embodiments, this component when combined with the orientation measurement given by the magnetometer determines the components of the force acting parallel and perpendicular to the writing plane. This sensor may act both as an activator for enabling other functions as well as for recording the magnitude of the actual writing force applied by the user of the writing surface.

In examples, the tip force sensor 36 or pen-writing surface contact sensor may be a Time-of-Flight (ToF) or proximity sensor.

The pen hardware 32 of the writing instrument 30 may further include a grip force sensor 38. One or more flexible pressure sensing pads may be wrapped around a tubular-shape of a main pen body, used to capture the distribution of the gripping forces applied by the user.

The flexible pressure sensitive pads can be either force resistive sensors that allow detection of squeezing or force sensitive resistive matrix sensor comprising an array of force sensing cells arranged in rows and columns. This configuration allows for measuring both the magnitude of the force applied as well as the location, resulting in a force distribution output mapping the gripping action.

In embodiments, the size of the sensor matrix does not exceed 50×75 mm.

In embodiments, the measured force resolution may range between 75 g and 2.5 kg.

In embodiments, a resolution of 1%, a device rise time above 10 kHz and a lifecycle of more than a million activations is considered for the operation.

The pen hardware 32 of the writing instrument 30 may further include an accelerometer/IMU 40.

At least one accelerometer, gyroscope or combination in the form of an IMU and at least one magnetometer placed either on the same location as the IMU or at a different position inside the pen are used to capture the position, the orientation, the speed and the acceleration of the writing instrument 30.

The accelerometer and gyroscope sensors considered in the system are providing output for all the 3-axis of motion or 6 DoF (Degrees of Freedom).

In embodiments, the bandwidth for the accelerometer is selected to be between 20 to 100 Hz.

The pen hardware 32 of the writing instrument 30 may further include a microcontroller 42.

A microcontroller (MCU) may process and control all the sensors, circuits and functions of the smart pen and may be of conventional wearable type or may be able to perform advanced AI processing. It may contain a flash memory module.

Microcontroller may be a conventional ultra-low power MCU suitable for wearable applications such as but not limited, a 16 or 32-bit-ARM MCU. Alternatively, the microcontroller may be based on a platform such as customizable single-chip ASIC AI or be based on a RISC-V AI architecture. The microcontroller may have a custom operating firmware. The memory unit allows both for temporary storage of generated data until transfer to the logging device for offline processing as well as for online processing.

The pen hardware 32 of the writing instrument 30 may further include a power source 44. The power source 44 can be power the electronic components of the smart pen and can include one or more disposable batteries, plug-in rechargeable batteries, and/or a wireless inductive charging module. The power source and the associated electronic circuit may be capable of delivering up to 12 V and in an example 3 V.

The pen hardware 32 of the writing instrument 30 may further include network capability 46 especially wireless network capability.

Wireless connectivity enables the smart pen to interact with other devices. The network capability 46 may support at least one of the different wireless protocols such as Wi-Fi, ANT+, Bluetooth Low Energy (BLE), IEEE 802.15.4.

The pen hardware 32 of the writing instrument 30 may further include operation buttons 48.

The control or operation buttons 48 can be located on the sides or on the periphery of the smart pen and their type can be one of the following:

Touch buttons

Switches

Rotation

Sliding

In embodiments, the smart pen may lack physical buttons and have its operation controlled by gestures, voice commands and/or is remotely controlled via another device such as PC, notebook, tablet, smartphone, smartwatch etc.

The pen hardware 32 of the writing instrument 30 may further include a magnetometer 50.

The use of magnetometers in a smart pen is to measure the writing angle between the writing instrument and the writing plane or surface. Tracking of the pen's orientation and/or direction enables the assessment of the user's hand rigidity and tremor.

In embodiments, the accuracy as well as the precision of the magnetometer sensor may be below 0.2 mm to capture accurately the position of the pen in space, while the orientation output may be less than 0.5°.

In embodiments, its size does not exceed 5.0×5.0×5.0 mm.

The pen hardware 32 of the writing instrument 30 may further includes a time-of-flight sensor 52 which may be an alternative to the tip force sensor 36 or writing surface contact sensor.

The time-of-flight sensor 52 or proximity sensor can be placed on the outer shell of the writing instrument, used to track the hovering distance of the pen during writing. One or more time-of-flight sensors 52 can be incorporated in the smart pen or writing instrument 30 either single or multi zone, with a field of view not less than 60° and a range up to 250 mm.

The Time-of-Flight (ToF) sensor is used for measuring the distance between the pen and the writing surface, based on the time difference between the emission of a signal and its return to the sensor, after being reflected by the writing surface. Various types of signals (also called carriers) can be used with the Time-of-Flight principle, the most common being sound and light.

The writing instrument 30 may further include a human machine interface (HMI) output like for example a notification LED.

One or more notification LED may be placed on the pen's body. These may be used to notify the user of the different operations performed by the pen, it's operational status, battery life, memory status, data transfer as well as suggest him/her to seek medical assistance.

In embodiments, the notification may be achieved by different colors of the LED and/or by different flash patterns.

In embodiments, the visual notification may be accompanied by audio or haptic feedback signals.

In embodiments, the at least one LED light source is considered for the following purposes:
- as an element of interaction with the user to indicate the operational status of the device (on/off),
- writing operation (contact of the pen with the writing surface),
- battery health and/or status,
- memory storage status,
- handwriting disorder notification.

The operation or execution of the methods and/or algorithms may be on the writing instrument 30 or on another operating device like e.g., a tablet, a smartphone, a smartwatch, a PC or any other suitable device capable of running the operation and visualisation application. The operating device is capable of wireless communication with the smart pen sending and receiving data.

In embodiments, the operating device may include, one or all the required algorithms and software for the processing and calculation of the data of the smart pen.

In embodiments, the operating device may include the user interface with which the user may interact with the smart pen and visualise the measurement results.

In embodiments, the operating device may alert the user in case of abnormal measurement data.

The pen software 34 of the writing instrument 30 can also be phrased as hand movement disorder evaluation software capable of calculating hand movement properties related to tremor and hypokinetic movement and evaluating whether they are normal or abnormal. One, some or all of the hand movement disorder evaluation software elements may be embedded in the smart writing instrument 30 or in the accompanying operating device.

The pen software 34 is described below. Where appropriate, reference is made to FIG. 2, which illustrates a process flow diagram 100 of a writing instrument 30 according to the present disclosure.

The hand movement disorder evaluation software or pen software 34 may include or consist of the following elements.

Figure 2:
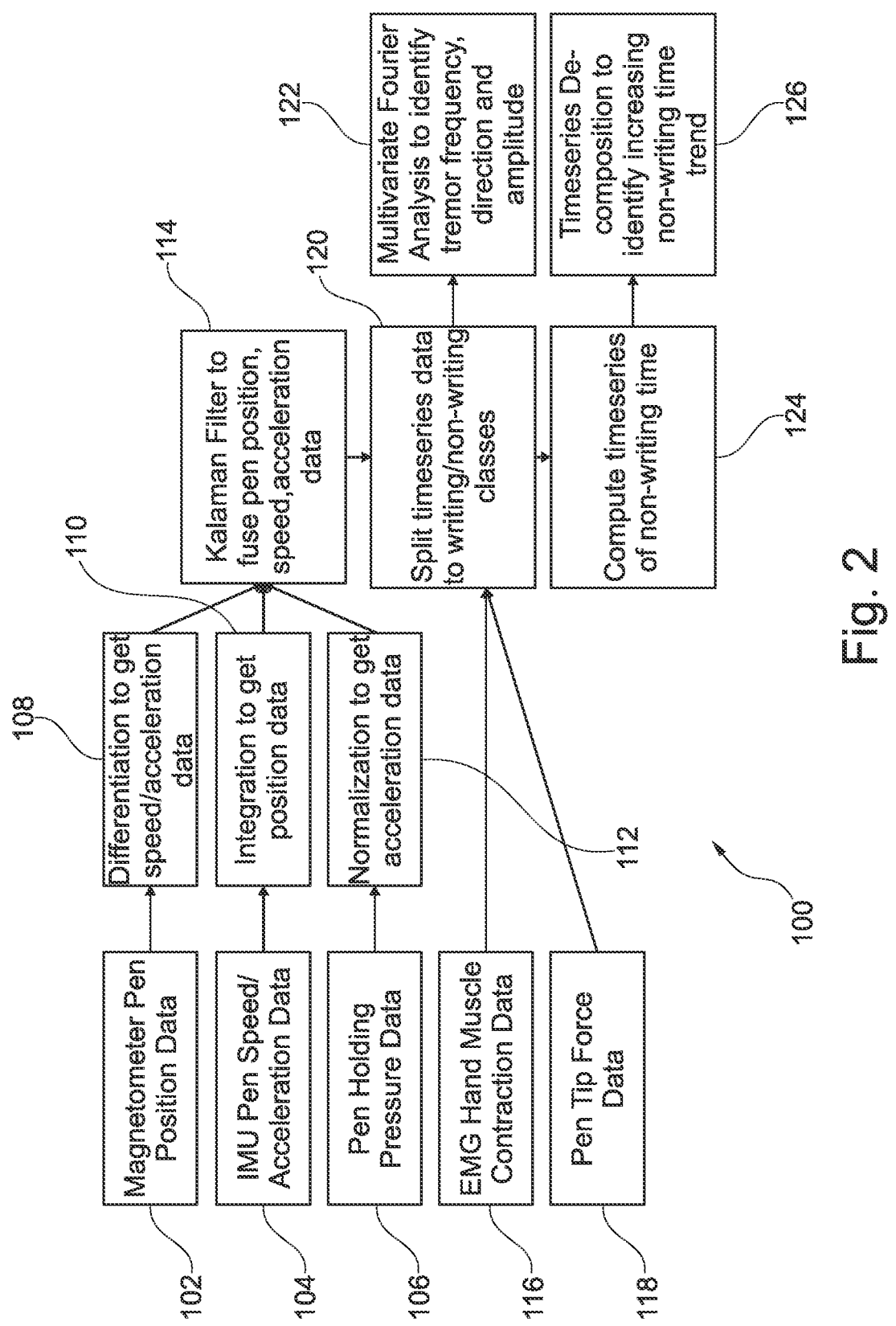
FIG. 2 illustrates a process flow diagram of a writing instrument according to the present disclosure.

The pen software 34 of the writing instrument 30 includes a data differentiation and integration algorithm 54 which may include steps 108, 110 and 112 of FIG. 2.

This is an algorithm that takes as an input the magnetometer pen position data 102, the IMU speed/acceleration data 104, and the pen holding pressure data 106, and performs the necessary conversions between location, speed, acceleration and force measurements. In particular, the magnetometer positional data are differentiated 108 to acquire speed and acceleration. The IMU data are differentiated e.g., integrated 110 to get speed and location, while, lastly, the pressure data are normalized 112 per unit of area and converted to force and then to acceleration, speed and location via Newton's law.

In embodiments, the raw data timeseries comprise a minimum sampling rate of 200 Hz and a maximum sampling rate of 1000 Hz. The rate is not changed during pre-processing. All these timeseries are inputted to the next algorithm for further analysis.

The pen software 34 of the writing instrument 30 further includes a data fusion algorithm 56 which may correspond to the Kalman filter 114 of FIG. 2.

This is an algorithm that takes as input processed data (location, speed, acceleration by two or more data sources) from the differentiation and integration algorithm 54 and fuses them e.g., through a Kalman filter to achieve better resolution and accuracy. For each timestep, three 3-dimensional vectors of location, speed, and acceleration originating from the magnetometer 50, IMU 40 and grip force sensors 38 are present. A multivariate Kalman filter combines these three vectors per timestep to get the final estimated vector. The covariance matrices are assumed to be gaussian. Parameter estimation is performed online via maximum likelihood estimation.

The integration of data from multiple sources can lead to the extraction of robust indicators for tremor and writing speed. In both cases, a sensor fusion methodology is adopted to combine motion information from the various sensors.

A (Non-)Writing-time classification algorithm 120 of FIG. 2 which is not depicted in FIG. 1 may be part of the data fusion algorithm 56 or may be working on outputs of the data fusion algorithm 56. The fused timeseries data are then split into writing and non-writing classes. This is done by utilizing the pen tip's force data 118. In particular, the continuous force values are binarized, using a small threshold of 0.1 to 0.2 N. Any value below that threshold is translated as the pen being on the air, while the rest that the pen in on the writing surface. This binary timeseries is then used as a filter to for the location, speed and acceleration timeseries, to keep only the writing timesteps.

For tremor analysis, the focus is placed on writing timeseries data since there is a correlation with a specific output, while non-writing data may include a wider range of motions, such as moving the pen around while thinking that highly differ from person to person and even for the same person depending on various conditions.

On the other size, non-writing time is of major importance for the evaluation of bradykinesia, since a gradual increase of non-writing time is indicative of that issue.

The pen software 34 of the writing instrument 30 further includes a tremor detection algorithm 58 which could also be named tremor detection and evaluation algorithm 122.

This is an algorithm that takes as an input the fused pen position, acceleration and speed data, as computed in the previous steps, and performs e.g., Fourier analysis to identify tremor frequency, direction and amplitude. Data from x, y and z directions are analyzed independently via fast Fourier transformation (FFT). Of main interest is the existence of tremor in the axis perpendicular to the direction of writing. As such, the linear combination of directions that equates to that perpendicular axis is calculated. Then the average primary frequency of location, speed and acceleration, as well as the standard deviation, are computed.

Further, the analysis is enhanced with an extra data source capturing hand tremor, through the use of the ElectroMyo-Graphy (EMG) muscle activation data 116. The corresponding signal analysis is performed on the EMG data to extract Root Mean Square (RMS) and Zero Crossings (ZC) features. FTTs of these features are also computed and the weighted average of the primary frequency is computed by combining the pen motion related variables and the arm motion related variables. A tremor frequency of 4-6 Hz with medium amplitude is identified as related to Parkinson's disease.

The pen software 34 of the writing instrument 30 may further include a hand motion detection algorithm 60 which could also be named hand movement detection and evaluation algorithm.

This is an algorithm 124 that takes as an input the fused pen position, acceleration and speed data and identifies with accuracy the hypokinetic hand movement properties. Patients that suffer from PD are reported to write and draw slowly, producing small handwriting and spirals formed with tightly bunched turns.

The primary objective is the evaluation of non-writing time evolution 126. After performing the algorithmic steps 108 to 114 and 120, the duration of non-writing time is quantified. A regression model is then fitted to the (time, non-writing duration) data using linear least squares. The coefficient of the fitted model is indicative of the pattern of increase/decrease of non-writing duration with time. When the coefficient is positive, it means that this duration increases as the time passes by.

A case-control study between healthy individuals and patients suffering from PD may support identification of the coefficient values that are suggestive of the disease. Further, the movement smoothness parameter can be calculated. Smoothness can be measured, using the spectral arch length (SAL) of movement speed profile as an appropriate index of movement fluidity. SAL can account for the change in the number of submovements and the inter-submovement interval, which are movement features influenced by bradykinesia. To compute smoothness, it is not necessary to filter data because of the inherent low-pass filtering action performed. Specifically, SAL is computed within the frequency range 0-4 Hz of the speed profile in each movement cycle and in each single movement.

The pen software 34 of the writing instrument 30 further includes operation and visualization software 62.

This is a software that takes the results of the system algorithms and visualises them to the user in order to alert him of normal or abnormal hand tremor and movement conditions.

It also permits the user to set specific parameters of the measurement sensors and communicate them to the smart pen.

The electromyography, EMG, unit 20 or EMG band extension includes an electromyography sensor 22 and a wired or wireless network capability 24.

The electromyography sensor 22 may be a surface electromyography sensor. The electromyography sensor 22 may include one or more flexible surface EMG compact and non-invasive skin adhering electrodes which are used to measure superficial muscle electrical activity and identify hand or finger movement disorders.

Flexible EMG sensors can be at least one of textile surface grids of electrodes, electrode skin probes or nap electrodes.

The electrodes can be simple disk electrodes adhering to the skin or they can be embedded in a flexible textile and/or polymer surface having the form of a patch that can adhere to a part of the palm or the hand or a glove that can be worn on the hand. The patch or glove design may be such that the electrodes can be placed accurately over the intrinsic hand muscles. The flexible patch or glove design may be considered as an extension of smart pen body.

In embodiments, the electrodes may be embedded in a smart band that can be worn on the forearm in order to measure signals from the extrinsic hand muscles. The smart band may be connected to the smart band through an electrical wire.

In embodiments, an amplifier circuit of the surface EMG signals may be incorporated in the electrode setup or incorporated in the smart pen.

In embodiments, EMG electrodes may be made but not limited, of Ag/AgCl, Ag, AgCl or Au.

In embodiments, the diameter of the electrodes may range from 2 mm to 2 cm.

In embodiments, the electrodes may be set at a monopolar or a bipolar setup to reduce crosstalk.

In embodiments, the myoelectric activity appears on the surface of the skin as electric potentials with limited bandwidth, from 15 to 400 Hz, and with very small amplitude, from some micro-Volts to a few milli-Volts peak-to-peak, depending on the intensity of muscle contraction.

The wired or wireless network capability 24 is configured to communicate with the network capability 46 of the writing instrument 30.

The electrodes of the electromyography, EMG, unit 20 may be connected with wires to the top of smart pen body either through a fixed connection or through a jack connector and a jack socket located at the top or a side of the smart pen.

In embodiments, the patch or glove or band may have wireless connection to the smart pen or to a standalone device.

Figure 3:
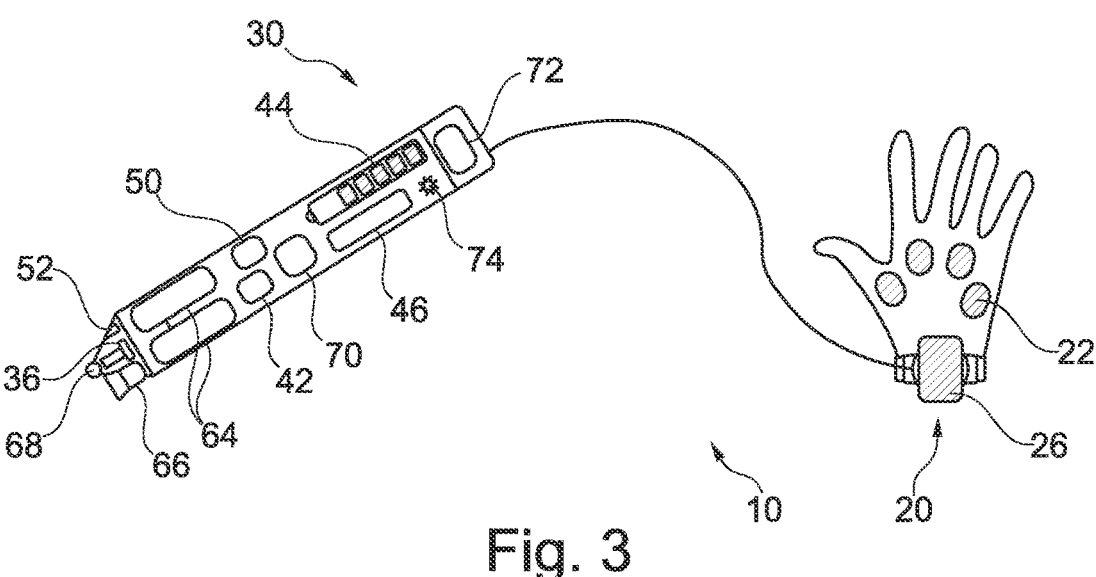
FIG. 3 illustrates a perspective view of a writing instrument according to the present disclosure.

FIG. 3 illustrates a perspective view of a system 10 according to the present disclosure. The system 10 can correspond to the system 10 as depicted in FIG. 1 and can include or execute the algorithm shown in FIG. 2.

The system 10 includes the writing instrument 30 and the EMG unit 20. The EMG unit 20 is connected with the writing instrument 30 by a wired connection. In other embodiments, a wireless connection is provided. The EMG unit 20 includes the base unit 26 to which at least one electromyography sensor 22 is connected. The base unit 26 includes the network capability 24 and may further include a computational unit for providing calculations on the raw data of the electromyography sensor 22.

The writing instrument 30 includes network capability 46 for communicating with the EMG unit 20. The writing instrument 30 further includes sensors like the tip force sensor 36, the grip force sensor 38 including flexible pressure sensing pads 64, the magnetometer 50, the IMU 40, the time-of-flight sensor 52 and in an example an optical sensor 66. The optical sensor 66 is arranged close to a tip 68 of the writing instrument 30 and can be used to capture handwriting details to support the algorithm.

The microcontroller 42 is connected with the sensors and adapted to execute the algorithm shown in FIG. 2. The memory unit 70 is connected to the microcontroller 42 and adapted to store raw data and computed data. An USB port 72 is further connected to the microcontroller 42 for external communication. An LED 74 can indicate the status of the writing instrument 30 and/or an indication to the user that his hand movements during the writing sessions are abnormal.

Figure 4:
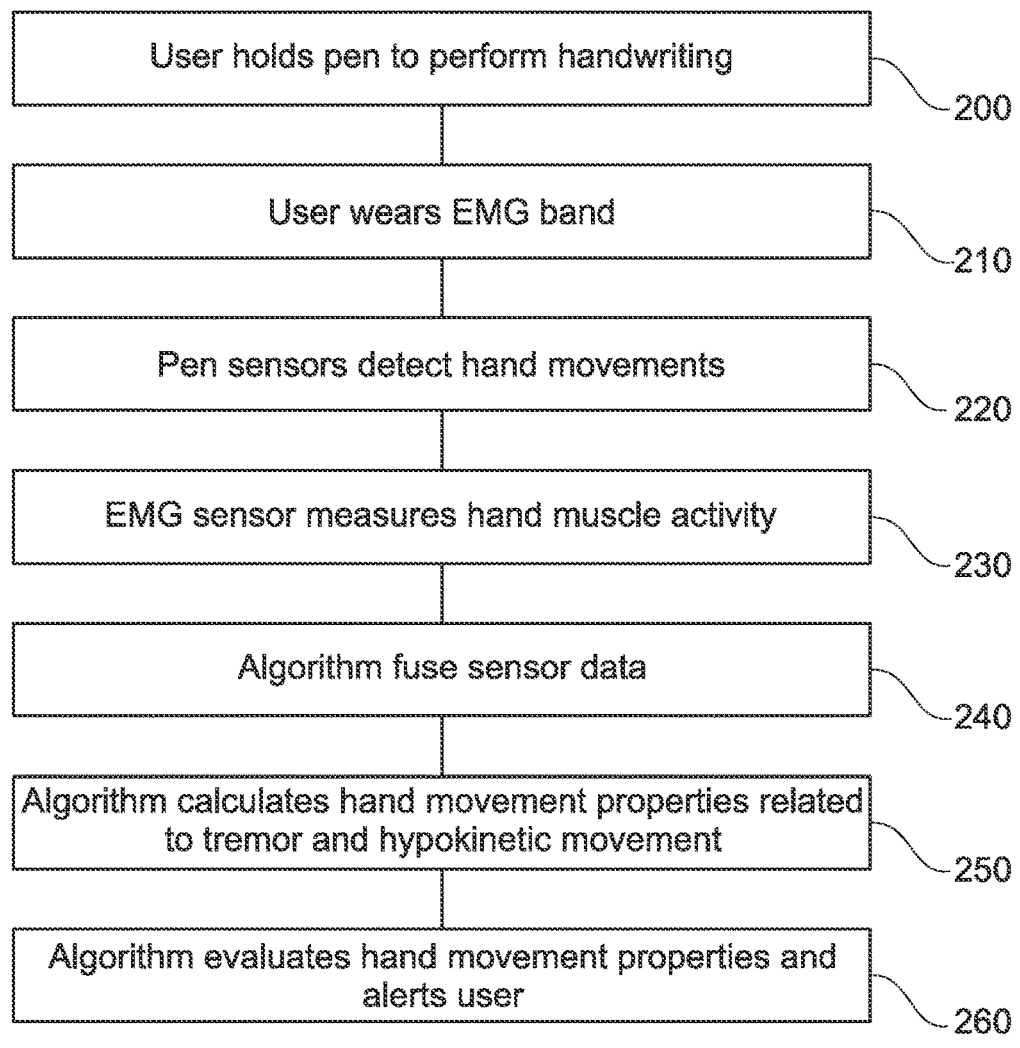
FIG. 4 illustrates a method flow chart for monitoring hand movements of a writing instrument's user according to the present disclosure.

FIG. 4 illustrates a method flow chart for monitoring hand movements of a writing instrument's user according to the present disclosure.

In a first step 200 of the method, a user takes the smart pen to perform handwriting or sketching.

In a second step 210, the user wears the EMG band on his hand/palm. In other words, the second step 210 includes providing an electromyography, EMG, sensor on the user's wrist or hand.

In a third step 220, sensors record hand movement data while the user performs handwriting and/or sketching activities during a writing session. In other words, the third step 220 includes monitoring hand movements of the user during a writing session with the writing instrument by reading sensors of the writing instrument.

The step of monitoring hand movements may include monitoring at least one of a writing force between the writing instrument's tip and a writing surface, motion information including position, orientation, speed, and/or acceleration of the writing instrument, and a force distribution and/or gripping strength applied by the user's fingers on the writing instrument.

The step 220 or the step 240 may include extrapolating a time span of the writing instrument not in contact with the writing surface between two consecutive writing strokes from the monitored writing force.

In a fourth step 230, the EMG sensor measure hand muscle activity of the user while the user performs handwriting and/or sketching activities during a writing session. In other words, the fourth step 230 includes monitoring hand muscle activity of the user during the writing session by reading the EMG sensor.

In a fifth step 240, the algorithms fuse sensor data. In other words, the fifth step 240 includes correlating hand motion data and hand muscle data obtained from the monitoring.

In a sixth step 250, the algorithm calculates hand movement metrics related to tremor and hand movement properties. In other words, the sixth step 250 includes evaluating the correlated data and classifying the hand movements as normal or abnormal.

One of steps 240 and 250 may include correlating and evaluating data includes computation of an average speed of the writing speed profile of writing identical words or sentences multiple times during a writing session.

In an example, historical data e.g., stored monitored data and/or related statistics may be included in this step as a comparison.

In a seventh step 260, the algorithm evaluates hand movement properties and alert user on whether they are normal or abnormal. In other words, the seventh step 260 includes providing an indication in case of an abnormal evaluation.

The steps 102 to 126 as depicted in FIG. 2 can be included in the method of FIG. 4.

The present disclosure also relates to the computer-implemented method for monitoring hand movements of a writing instrument's user and the system for monitoring hand movements of its user of the following aspects:

1. A computer-implemented method for monitoring hand movements of a writing instrument's user, comprising:
   providing an electromyography sensor on the user's wrist or hand;
   monitoring hand movements of the user during a writing session with the writing instrument by reading sensors of the writing instrument;
   monitoring hand muscle activity of the user during the writing session by reading the electromyography sensor;
   correlating hand motion data and hand muscle data obtained from the monitoring;
   evaluating the correlated data and classifying the hand movements as normal or abnormal based on at least one of tremor parameters, hypokinetic parameters, and historical data of the user; and
   providing an indication in case of an abnormal evaluation.

2. The method of aspect 1, comprising:
   storing monitored data and/or related statistics as historical data.

3. The method of one of the preceding aspects, wherein monitoring hand movements includes monitoring at least one of a writing force between the writing instrument's tip and a writing surface, motion information including position, orientation, speed, and/or acceleration of the writing instrument, and a force distribution and/or gripping strength applied by the user's fingers on the writing instrument.

4. The method of aspect 3, wherein monitoring hand movements includes:
   extrapolating a time span of the writing instrument not in contact with the writing surface between two consecutive writing strokes from the monitored writing force.

5. The method of one of the preceding aspects, wherein monitored data is aggregated into motion profiles of the hand movements, wherein the motion profiles are at least one of position, speed, or acceleration of the writing instrument.

6. The method of one of the preceding aspects, comprising:
   his hand movements
   correlating and evaluating data, includes computation of an average speed of the writing speed profile of writing identical words or sentences multiple times during a writing session.

7. The method of one of the preceding aspects, wherein correlating includes:
   fusing hand motion data through a data processing algorithm, wherein the hand motion data has the form of a 3-dimensional vector, wherein the dimensions are position, speed, and acceleration of the writing instrument.

8. The method of aspect 7, comprising:
   sorting the fused hand motion data into writing and non-writing parts by using data of a writing force between the writing instrument's tip and a writing surface.

9. The method of aspect 8, wherein evaluating includes:
   identifying at least one of tremor frequency, direction, and amplitude by performing a frequency domain Fourier analysis from at least one of x, y, and z directions on the writing parts of the fused hand motion data;
   performing a frequency domain analysis on root mean square and/or zero crossings features extracted from the hand muscle data; and
   computing a weighted average of the primary frequency by combining the variables obtained by the two prior steps.

10. The method of aspect 8, wherein evaluating includes:
    quantifying the duration of the non-writing parts;
    fitting a regression model to a non-writing duration; and
    assessing an increase of non-writing duration when the coefficient of the fitted regression model is positive.

11. The method of one of the preceding aspects, wherein the indication is provided via a wireless communication system to an external device having an interface.

12. A system for monitoring hand movements of its user, comprising:

a writing instrument comprising:

one or more sensors configured to monitor hand movements of the user during a writing session with the writing instrument by reading sensors of the writing instrument;

a communication system configured to provide an indication in case of abnormal hand movements; and a computer system configured to execute the computer-implemented method for monitoring hand movements of a writing instrument's user according to one of the preceding aspects; and an electromyography sensor configured to be attached on the user's wrist or hand, wherein the electromyography sensor is in communication with the writing instrument.

13. The system of aspect 12, comprising:

a storage system configured to store generated data as historical data.

14. The system of aspect 12 or 13, comprising at least one of:

a hand presence sensor configured to obtain a force distribution and/or a gripping strength applied by the user's fingers on the writing instrument;

a force tip sensor configured to obtain a writing force between the writing instrument's tip and a writing surface;

at least one motion sensor configured to obtain at least one of position, orientation, speed, and acceleration of the writing instrument; and a proximity sensor configured to obtain a hovering distance of the writing instrument's tip above the writing surface.

15. The system of aspect 14, wherein the proximity sensor is a time-of-flight sensor, wherein the hand presence sensor comprises a plurality of flexible pressure sensing pads, wherein the force tip sensor comprises a force and/or pressure sensor configured to measure a force and/or pressure of a tip of the writing instrument, and/or wherein the at least one motion sensor comprises at least one of a magnetometer, a gyroscope, an accelerometer, and an inertial measurement unit.

16. The system of one of aspects 12 to 15, comprising:

a digitizing system configured to digitize written text of a writing session.

17. The system of one of aspects 12 to 16, the writing instrument comprising:

a user interface configured to receive input from a user and/or to provide information to the user such as the indication.

18. The system of one of aspects 12 to 17, the writing instrument comprising:

a wireless communication system configured to provide the indication via an external device having an interface.

The invention claimed is:

1. A computer-implemented method for monitoring hand movements of a user, comprising:

providing an electromyography sensor on the user's wrist or hand;

monitoring hand movements of the user during a writing session with the writing instrument by receiving hand motion data via at least one sensor of the writing instrument;

monitoring hand muscle activity of the user during the writing session by receiving hand muscle data via the electromyography sensor;

correlating the hand motion data and the hand muscle data obtained from the monitoring;

fusing hand motion data through a data processing algorithm, wherein the hand motion data has the form of a 3-dimensional vector, wherein the dimensions are position, speed, and acceleration of the writing instrument;

evaluating the correlated data and classifying the hand movements as normal or abnormal based on at least one of tremor parameters, hypokinetic parameters, and historical data of the user; and providing an indication in case of an abnormal evaluation.

2. The method of claim 1, comprising:

storing monitored data and/or related statistics as historical data.

3. The method of claim 1, wherein the hand movements further include at least one of a writing force between a tip of the writing instrument and a writing surface, motion information including position, orientation, speed, and/or acceleration of the writing instrument, and a force distribution and/or gripping strength applied by the user's fingers on the writing instrument.

4. The method of claim 3, wherein monitoring hand movements includes:

extrapolating a time span of the writing instrument not in contact with the writing surface between at least two consecutive writing strokes from the writing force.

5. The method of claim 1, wherein the hand motion data and the hand muscle data is aggregated into motion profiles of the hand movements, wherein the motion profiles are at least one of position, speed, or acceleration of the writing instrument.

6. The method of claim 1, comprising:

computing an average speed of a writing speed profile of writing identical words or sentences multiple times during the writing session.

7. The method of claim 1, comprising:

sorting the fused hand motion data into writing and non-writing parts by using data of a writing force between a tip of the writing instrument and a writing surface.

8. The method of claim 7, including:

identifying at least one of tremor frequency, direction, and amplitude by performing a frequency domain analysis from at least one of x, y, and z directions on the writing parts of the fused hand motion data;

performing the frequency domain analysis on root mean square and/or zero crossings features extracted from the hand muscle data; and computing a weighted average of a primary frequency by combining variables obtained by the identifying and performing steps.

9. The method of claim 7, including:

quantifying a duration of the non-writing parts; and fitting a regression model to the non-writing duration.

10. A system for monitoring hand movements of a user, comprising:

a writing instrument comprising:

one or more sensors configured to monitor hand movements of the user during a writing session with the writing instrument by reading sensors of the writing instrument;

a communication system configured to provide an indication in case of abnormal hand movements; and a computer system configured to execute computer-implemented steps for monitoring hand movements of the writing instrument's user, including fusing hand motion data through a data processing algorithm, wherein the hand motion data has the form of a 3-dimensional vector, wherein the dimensions are position, speed, and acceleration of the writing instrument; and an electromyography sensor configured to be attached on the user's wrist or hand, wherein the electromyography sensor is in communication with the writing instrument.

11. The system of claim 10, further comprising:

a storage system configured to store generated data as historical data.

12. The system of claim 10, wherein the one or more sensors include at least one of:

a hand presence sensor configured to obtain a force distribution and/or a gripping strength applied by the user's fingers on the writing instrument;

a force tip sensor configured to obtain a writing force between the writing instrument's tip and a writing surface;

at least one motion sensor configured to obtain at least one of position, orientation, speed, and acceleration of the writing instrument; and a proximity sensor configured to obtain a hovering distance of the writing instrument's tip above the writing surface.

13. The system of claim 12, wherein the proximity sensor is a time-of-flight sensor, wherein the hand presence sensor comprises a plurality of flexible pressure sensing pads, wherein the force tip sensor comprises a force and/or pressure sensor configured to measure a force and/or pressure of the tip of the writing instrument, and/or wherein the at least one motion sensor comprises at least one of a magnetometer, a gyroscope, an accelerometer, or an inertial measurement unit.

14. The system of claim 10, further comprising:

a digitizing system configured to digitize written text of the writing session.

15. The system of claim 10, the writing instrument further comprising:

a user interface configured to receive input from the user and/or to provide information to the user, wherein the information is the indication.

16. The system of claim 10, the writing instrument further comprising:

a wireless communication system configured to provide the indication via an external device having an interface.

17. The system of claim 10, wherein the computer-implemented steps comprise:

monitoring hand movements of the user during a writing session with the writing instrument by receiving hand motion data via the one or more sensors;

monitoring hand muscle activity of the user during the writing session by receiving hand muscle data via the electromyography sensor;

correlating hand motion data and hand muscle data obtained from the monitoring;

evaluating the correlated data and classifying the hand movements as normal or abnormal based on at least one of tremor parameters, hypokinetic parameters, and historical data of the user; and providing the indication in case of an abnormal evaluation.

18. The system of claim 17, wherein the computer-implemented steps further comprise:

computing an average speed of a writing speed profile of writing identical words or sentences multiple times during the writing session.

19. The system of claim 17, wherein the computer-implemented steps further comprise:

sorting the fused hand motion data into writing and non-writing parts by using data of a writing force between a tip of the writing instrument and a writing surface.

20. The system of claim 19, wherein the computer-implemented steps further comprise:

quantifying a duration of the non-writing parts; and fitting a regression model to the non-writing duration.

* * * * *